(12) United States Patent
Landa et al.

(10) Patent No.: US 7,816,310 B2
(45) Date of Patent: Oct. 19, 2010

(54) INCREASED MOISTURIZATION EFFICACY USING HYDROXYALKYLUREA AND AMMONIUM LACTATE

(75) Inventors: Peter A. Landa, Springfield, NJ (US); Hongjie Cao, Somerville, NJ (US); Gary T. Martino, Monmouth Junction, NJ (US); Irina M. Morosov, Newfoundland, PA (US); Tatiana Drovetskaya, Basking Ridge, NJ (US)

(73) Assignee: Akzo Nobel N.V., Arnhem (NL)

( * ) Notice: Subject to any disclaimer, the term of this patent is extended or adjusted under 35 U.S.C. 154(b) by 98 days.

(21) Appl. No.: 10/939,204

(22) Filed: Sep. 10, 2004

(65) Prior Publication Data

US 2005/0113269 A1 May 26, 2005

Related U.S. Application Data

(63) Continuation-in-part of application No. 10/723,340, filed on Nov. 26, 2003, now abandoned.

(51) Int. Cl.
*A61K 7/00* (2006.01)

(52) U.S. Cl. .................. 510/130; 510/119; 510/123; 510/499; 510/503

(58) Field of Classification Search .................. 510/130, 510/501; 424/70.1
See application file for complete search history.

(56) References Cited

U.S. PATENT DOCUMENTS

| | | | |
|---|---|---|---|
| 5,858,549 A | 1/1999 | Kielbania, Jr. et al. | |
| 5,880,076 A | 3/1999 | Vermeer | |
| 6,010,707 A | 1/2000 | Philippe et al. | |
| 6,093,412 A | 7/2000 | Philippe et al. | |
| 6,140,388 A | 10/2000 | Nass et al. | |

FOREIGN PATENT DOCUMENTS

| | | |
|---|---|---|
| DE | 27 03 185 | 1/1977 |
| DE | 27 03 185 | 8/1978 |
| EP | 0815829 A1 | 1/1998 |
| EP | 0 876 812 | 11/1998 |
| JP | 2001-309986 | 11/2001 |
| WO | WO 01/00170 | 1/2001 |

OTHER PUBLICATIONS

Partial English Translation of Japanese Publication No. 2001-309986.

*Primary Examiner*—Necholus Ogden, Jr.
(74) *Attorney, Agent, or Firm*—James C. Abruzzo

(57) ABSTRACT

A personal care composition having at least one hydroxyalkylurea (HAU) optionally in combination with at least one other moisturizing agent. The at least one HAU, alone or together with the at least one moisturizing agent, provides not only the perception of moisturization, but also actual increased moisturization efficacy. When the two are used in combination in a personal care composition, they are provided in a synergistically moisturizing effective ratio to provide that perception of moisturization and increased moisturization efficacy. Such personal care compositions provide an enhanced smooth feel as well as enhanced flexibility, elasticity, suppleness and firmness without leaving a heavy or greasy feel.

16 Claims, 3 Drawing Sheets

US 7,816,310 B2

INCREASED MOISTURIZATION EFFICACY USING HYDROXYALKYLUREA AND AMMONIUM LACTATE

CROSS REFERENCE TO RELATED APPLICATIONS

The present application is a continuation-in-part of U.S. application Ser. No. 10/723,340, filed 26 Nov. 2003 now abandoned.

BACKGROUND OF THE INVENTION

1. Technical Field

The present invention relates to personal care compositions. More specifically, the present invention relates to personal care compositions that use hydroxyalkylurea for providing improved moisturization efficacy. In another aspect, the present invention relates to personal care compositions that use hydroxyalkylurea in combination with other moisturizing agents in a synergistically moisturizing effective ratio, thereby providing increased moisturization efficacy.

2. Background Information

A significant segment of the global population uses products to moisturize their skin and hair, and such segment continues to grow at a substantial rate. Unfortunately, many of these products do not actually moisturize. Instead, they simply give the appearance of moisturization by reducing fine lines and/or flaking and adding shine. When trying to provide or increase moisturizing efficacy, many of the moisturizing products currently on the market also leave a heavy, greasy feel that consumers find undesirable.

The use of hydroxyalkylurea in personal care compositions is known in the art. For example, U.S. Pat. No. 5,858,549 discloses compositions that utilize hydroxyalkylurea crosslinking agents on natural or synthetic substrates or in the preparation of coatings. Hydroxyalkylureas are also used in thermosetting binders (see, e.g., U.S. Pat. No. 6,140,388), in personal care products and detergent compositions (see, e.g., U.S. Pat. No. 5,880,076 and German Patent No. 27 03 185). However, none of these patents disclose the use of hydroxyalkylurea either alone or in combination with other moisturizing agents to increase the moisturizing efficacy of personal care compositions.

Accordingly, there is a need for personal care compositions with improved moisturizing efficacy.

SUMMARY OF THE INVENTION

It has now been found that personal care compositions that include hydroxyalkylurea alone or in combination with other moisturizing agents provide not only the perception of moisturization, but also actual increased moisturization efficacy. Such personal care compositions provide an enhanced smooth feel as well as enhanced flexibility, elasticity, suppleness and firmness without leaving a heavy, tacky or greasy feel.

The present invention relates to a personal care composition having at least one hydroxyalkylurea optionally in combination with at least one other moisturizing agent, which provides not only the perception of moisturization, but also actual increased moisturization efficacy. Such personal care compositions provide an enhanced smooth feel as well as enhanced flexibility, strength, elasticity, suppleness and firmness without leaving a heavy, tacky or greasy feel.

When provided together in a personal care formulation, the hydroxyalkylurea and the moisturizing agent are present in a synergistically moisturizing effective ratio. In one aspect, the ratio of hydroxyalkylurea to moisturizing agent is at least about 0.5:15.0 and no more than about 15.00:0.05. In another aspect, the ratio of hydroxyalkylurea to moisturizing agent is at least about 1:5 and no more than about 5:1. In one embodiment, the hydroxyalkylurea is N-2-hydroxyethylurea. The amount of hydroxyalkylurea is found in the personal care composition is present in an amount of from about 0.5% to 15.0% by weight of the composition. In another aspect, hydroxyalkylurea is present in an amount of from about 1 to 8% by weight of the personal care composition.

Moisturizers useful in personal care compositions that provide the improved moisturization efficacy when used in combination with hydroxyalkylurea include petrolatum, mineral and vegetable oils, lanolins, glycerin, sorbitol, polyols, urea, lactic acid, lactates, sugars, alpha hydroxy acids, beta hydroxy acids, sodium hyaluronate, hyaluronic acid, pyrrolidone carboxylic acid. The moisturizer(s) can be present in an amount of from about 0.5% to 15% by weight of the personal care composition. In another aspect, the moisturizer is present in an amount of from about 1% to 10% by weight of the personal care composition. In even another aspect, the moisturizer is present in an amount of from about 2% to about 6% by weight of the personal care composition.

In one embodiment of the present invention, the hydroxyalkylurea is N-2-hydroxyethylurea and the moisturizer is selected from the group consisting of petrolatum, mineral and vegetable oils, lanolins, glycerin, sorbitol, polyols, urea, lactic acid, lactates, sugars, alpha hydroxy acids, beta hydroxy acids, sodium hyaluronate, hyaluronic acid, pyrrolidone carboxylic acid, and combinations thereof.

Personal care compositions according to the present invention can include, e.g., skin care compositions, hair products and conditioners. Hair products according to the present invention can include, e.g., hair gel, hair lotion, hair cream, mousse, shampoo, conditioner and hair spray. Conditioners according to the present invention can include, e.g., leave-on conditioners, including leave-on hair and skin conditioners.

The present invention also relates to a personal care composition having at least one hydroxyalkyl urea and at least one ammonium salt, wherein the hydroxyalkyl urea and the ammonium salt are present in a synergistically moisturizing effective ratio.

In addition to the above compositions, the present invention provides a process for preparing such compositions. This process includes reacting at least one ethanolamine with urea to form hydroxyalkylurea. Any residual ammonia is neutralized with a cosmetically suitable acid to form an ammonium salt. The cosmetically suitable acid includes, e.g., lactic acid, glycolic acid, citric acid, maleic acid, acetic acid, salicylic acid and combinations thereof.

In another aspect, the present invention provides for a hair moisturizing composition having at least one hydroxyalkylurea.

The terms below have the following meanings as used herein—

The term "surfactant" means an ingredient that is used in a cosmetic formulation and exhibits the ability to reduce the interfacial tension between two immiscible substances, wets skin and hair surfaces, emulsifies or solubilizes oils, and/or suspends soil and is meant to include amphoteric, anionic, cationic, and nonionic surfactants.

The term "mousse" means a personal care product in which the ingredients foam when dispensed from their container without any mechanical action from the user except possibly the shaking of the product in the container prior to actuation of a valve and subsequent dispensing of the internal contents by actuation.

The term "shampoo" means a cleansing product containing surfactants that is massaged into wet hair, usually thereby creating foam, which is then rinsed from the hair with water, removing at least some soil and/or oils from the hair.

The term "hair lotion" means a composition below 20,000 centipoise at 25° Celsius ('C.') and standard pressure that is applied to hair to provide a cosmetic benefit.

The term "hair cream" means a composition equal to or greater than 20,000 centipoise at 25° C. and standard pressure that is applied to the hair to provide a cosmetic benefit.

The term "cosmetic benefit" includes, but in no way is limited to, such benefits as moisturizing, sun protection, fragrance, wrinkle reduction, and tanning.

DETAILED DESCRIPTION OF THE INVENTION

Figure 1:
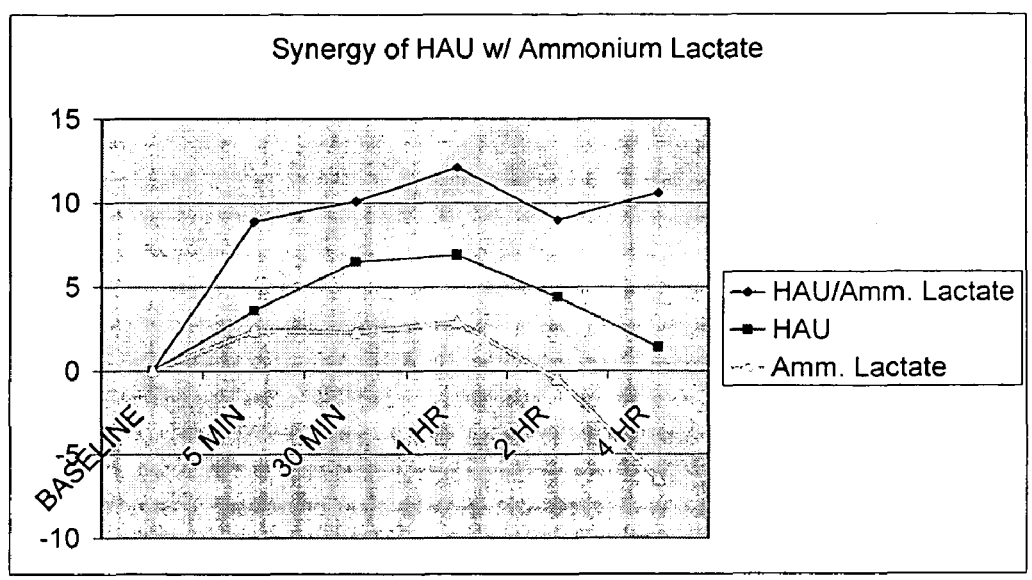
FIG. 1 depicts the relative skin moisture content of the synergy between hydroxyalkylurea and ammonium lactate at a ratio of 5.00:0.05.

The present invention relates to a personal care composition comprising at least one hydroxyalkylurea optionally in combination with at least one other moisturizing agent, which provides not only the perception of moisturization, but also actual increased moisturization efficacy. Such personal care compositions provide an enhanced smooth feel as well as enhanced flexibility, strength, elasticity, suppleness and firmness without leaving a heavy or greasy feel.

Hydroxyalkylureas, as used herein, are derived from urea and are of the general formula:

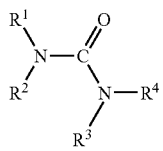

wherein $R^1$, $R^2$, $R^3$ and $R^4$ each independently represent hydrogen, a $C_{1-4}$ alkyl or a $C_{2-6}$ hydroxyalkyl group that can contain from 1 to 5 hydroxyl or hydroxyalkyl groups providing that at least one of the radicals $R^1$-$R^4$ is a hydroxyalkyl or oligohydroxyalkyl group. An example of a particularly useful hydroxyalkylurea is N-2-hydroxyethylurea having the structure

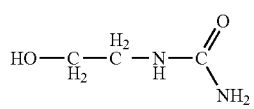

Personal care compositions according to the present invention can also include at least one moisturizing agent. Such moisturizing agents are known in the art and include without limitation occlusion compounds such as petrolatum, mineral oils, vegetable oils, triglycerides, lanolins and their derivatives, unsaturated fatty acids and their derivatives, silicones, and some emollients; humectants such as glycerin, sorbitol, lactates (including, but not limited to sodium, ammonium, and potassium salts), polyols (e.g., propylene glycol), polyethylene glycol (PEG 200-600), and Sorbeth-30; natural moisturizing factors (NMFs) such as urea, lactic acid, and sodium pyrrolidone carboxylic acid (NaPCA); liposomes, natural and vegetal moisturizing agents such as glycerin, serine, chitosan PCA, sodium hyaluronate, hyaluronic acid, microsponges, soluble collagen, modified protein, sugars, monosodium L-glutamate, lecithins and phospholipids and their derivatives; α- and β-hydroxy acids such as glycolic acid, lactic acid, citric acid, maleic acid and salicylic acid; polymeric moisturizers such as polysaccharides and their derivatives such as modified starch, xanthan gum and dehydroxanthan gum, polyacrylates, and polyquaternium-4, -10 and -51; and amino acids such as glutamic acid, aspartic acid, and lysine. As used herein, all acids are intended to include the salts thereof. Particularly suitable moisturizers are petrolatum, mineral and vegetable oils, lanolin, glycerin, sorbitol, polyols, urea, lactic acid, lactates (including but not limited to sodium, ammonium, and potassium salts), α- and β-hydroxy acids, sodium hyaluronate, hyaluronic acid, sugars, and pyrrolidone carboxylic acid (PCA).

The personal care composition can also include other optional ingredients found in such formulations that are commonly used in the industry. These can vary greatly depending upon the type of composition (e.g., skin care or hair care) and the functionality and properties desired. Without limitation, these components include emulsifiers, aesthetic modifiers, UV filters, humectants, moisturizers, emollients, solvents, chelating agents, vitamins, antioxidants, botanical extracts, pH adjusting and neutralizing agents, polymers, surfactants or soaps, thickeners, preservatives, fragrances, active ingredients (such as anti-aging agents, firming or toning agents, etc.), dyes and pigments.

The hydroxyalkylurea of the present invention is compatible with most other components used in conventional personal care compositions. For example, cosmetic compositions may contain one or more other components such as moisturizers, UV filters (both organic and inorganic UV actives), conditioning agents, emulsifiers, pH adjusters and neutralizers, emollients, solvents, antioxidants, vitamins, styling agents, chelating agents, preservatives and fragrances. Skin care and cosmetic compositions can also contain at least one component selected from the group consisting of vitamins, anti-aging agents, moisturizers, emollients, emulsifiers, surfactants, opacifiers, foaming agents, preservatives, antioxidants, pigments, dyes and active ingredients.

In one aspect, the hydroxyalkylurea of the present invention is present in a moisturizing effective amount. Understandably, this amount can vary depending any number of factors, for example, the type and amount of other moisturizing agents and the type of personal care composition in which it is included. In one aspect, the hydroxyalkylurea is present in an amount of from about 0.25 to about 15.0% by weight of the personal care composition. In another aspect, the hydroxyalkylurea is present in an amount of about 1 to about 8% by weight of the composition. In one aspect, the hydroxyalkylurea is present in an amount of about 1.5 to about 5% by weight of the personal care composition.

In another embodiment, a moisturizing agent is present with the hydroxyalkylurea in a moisturizing effective amount. This amount can vary depending upon a variety of factors such as the type of moisturizing agent, the amount of hydroxyalkylurea, and the type of personal care composition in which it is to be included. In one embodiment, the moisturizing agent is present in an amount of from about 0.002 to about 15% by weight of the personal care composition. In another embodiment, the moisturizing agent is present in amount of from about 0.1 to about 10% by weight of the personal care composition. In one embodiment, the moisturizing agent is present in an amount of from about 0.5 to about 6% by weight of the personal care composition.

When the hydroxyalkylurea is used in combination with a moisturizing agent according to one embodiment of the present invention, the ratio of hydroxyalkylurea to moisturizing agent is preferably in a synergistically moisturizing effective ratio. In one embodiment, the ratio is between about 0.25:0.00 and about 20.0:0.0 hydroxyalkylurea to moisturizing agent. In one embodiment, the ratio is between about 0.5:15.0 and about 15.0:0.05 hydroxyalkylurea to moisturizing agent. In another embodiment, the hydroxyalkylurea to moisturizing agent ratio is between about 1:5 and about 15.00:0.05. In another embodiment, the ratio is between about 0.5:15.0 and about 5:1 hydroxyalkylurea to moisturizing agent. In another embodiment, the hydroxyalkylurea:moisturizing agent ratio is between about 1:5 and about 5:1.

This combination of hydroxyalkylurea and moisturizer produces a synergistic relative moisturization efficacy. Thus, the combination has an increased moisturization efficacy over that expected, even more than the added moisturization efficacy of the individual components alone.

Methods of manufacturing hydroxyalkylureas are known in the art. One known method is by reacting at least one ethanolamine with urea (1:1 molar concentrations) at elevated temperatures of about 80° C. to 200° C. with adequate sparging. Using this method, residual levels of about 0.1 to 1% ammonia are typically produced and remain in solution. The ammonia can be neutralized with any cosmetically suitable acid to form an ammonium salt. This ammonium salt and hydroxyalkylurea also produce a synergistic moisturization efficacy. Particularly suitable acids include lactic acid, glycolic acid, citric acid, maleic acid, acetic acid, and salicylic acid.

Personal care compositions include without limitation skin moisturizing lotions and creams including for the face and body, moisturizing cleansers and soaps, anti-aging products, nourishing creams and lotions, firming and toning products, shaving creams, deodorants, color cosmetics including foundations, makeups, and lipsticks, suncare products such as sunscreens, suntan lotions, and after-sun products, hair conditioners and cream rinses, and shampoos, hair styling products including hairsprays, gels, and mousses, personal care wipes, baby care products, hair dyes, hair permanent wave, anti-frizz, volumizing, and bath and shower products. Particularly suitable compositions are skin care compositions.

The personal care compositions comprising both hydroxyalkylurea and moisturizer not only have improved moisturization efficacy, but also provide improved aqueous and emulsion freeze-thaw stability. Further, such compositions have a non-tacky, nongreasy feel when applied.

EXAMPLES

The following examples are presented to further illustrate and explain the present invention and should not be taken as limiting in any regard. All percentages used are on a weight/weight basis.

In the examples below, the following procedures/tests are used

Skin Moisturization (Hydration). Aqueous solutions (along with formulated lotions) were applied to the volar forearm of panellists with dry skin. Solutions tested contained between 2.5 and 15% active levels of Hydroxyalkylurea and various moisturizing agents. The various individual moisturizing agents were also used in combination with Hydroxyalkylurea and the relative moisture contents in the skin were compared.

Moisture levels were measured using a Corneometer® CM 825 (available from CK Industries) prior to and at various time intervals after application of forty microliters of each sample (Temperature ~21° C., Relative Humidity ~35%).

Hair Moisturization. Moisture retention/uptake on hair was determined using two test methods—a 'Dynamic Vapor Sorption' (DVS) technique and a 'Controlled Humidity Hair Moisturization Analysis'. 50% active aqueous solutions were applied to hair in both test methods.

In the Controlled Humidity Hair Moisturization Analysis, moisture uptake and retention of the different test samples were compared using hair swatches weighing approximately 4 grams and measuring 1.27 cm in width and 25.4 cm in length. Each test sample solution was evaluated in triplicate. An initial weight ($w_i$) was taken for each swatch. Next, the swatches were soaked for 1 hour in 30 ml of the test solution (50% active). After removal from the test solution, excess product was squeezed off using the analyst's thumb and forefinger and then reweighed ($w_{wet}$). The swatches were then dried in a 49° C. oven for 1.5 hours and weighed ($w_{dry}$) again. The weight of active deposited on the hair after the water has evaporated ($w_{active}$) is the difference between $w_i$ and $w_{dry}$.

In order to ensure removal of all moisture from the samples, the treated hair swatches were then placed in a vacuum oven at 45° C. and −100 kPa (−30 mmHg) for 20 hours. After drying, the swatches were hung on curl retention boards and placed in a humidity chamber at 37° C. and 85% relative humidity for 20 hours. The swatches were reweighed ($W_{HH}$) when removed from the humidity chamber. The difference between wi and $W_{HH}$ is the weight of moisture gained in the humidity chamber ($w_{HC}$) plus the weight of moisturizing active on the hair. The percent total weight gained ($w_{tot}$) is obtained by multiplying the quantity $w_{HC}$ divided by $w_i$ by 100.

After determination of the total weight gained, the swatches are returned to the vacuum oven at the same conditions given above for another 20 hours, then removed and weighed ($w_{final}$) for a final time. The difference between $w_{HH}$ and $w_{final}$ is the weight of moisture gained in the humidity chabinet ($w_{moist}$). The percent moisture gained is determined by multiplying by 100 the quantity $w_{moist}$ divided by $w_i$.

Moisture uptake was also determined using a Surface Measurement Systems Dynamic Vapor Sorption Analyzer 2000 (DVS). The testing was run on blonde damaged hair. The procedure used was as follows—

Approximately 0.3-0.4 grams of hair were weighed. About 11 grams of the 50% solution was added to a weigh boat. The weight of hair was then soaked in the solution in the weigh boat for an hour, and then dried in a 49° C. oven for 40 minutes. The hair sample was then wrapped around a small pre-weighed paperclip and put onto a microbalance in the DVS instrument test chamber. The instrument then brought the conditions in the test chamber to 85% relative humidity and 37° C. over 30 minutes. Once this target humidity was reached, it was held for 20 hours. The percent moisture uptake is equal to the percent increase in weight of the hair and was determined after 4 and 20 hours.

Example 1

Hydroxyethylurea (HAU) and the moisturizing agent ammonium lactate (Amm. Lactate), were analyzed alone and in combination. Active levels used for the individual agents were HAU at 5% and ammonium lactate at 0.05%. The combination consisted of a total of 5% moisturizing ingredients at a ratio of 5:0.05 of HAU:ammonium lactate. FIG. 1 shows the relative skin moisture content initially and at 5 minutes, 15 minutes, 1 hour, 2 hours, and 4 hours after application. From FIG. 1 it is seen that the blend provides a significant increase in moisture over either individual moisturizing agent alone.

Figure 2:
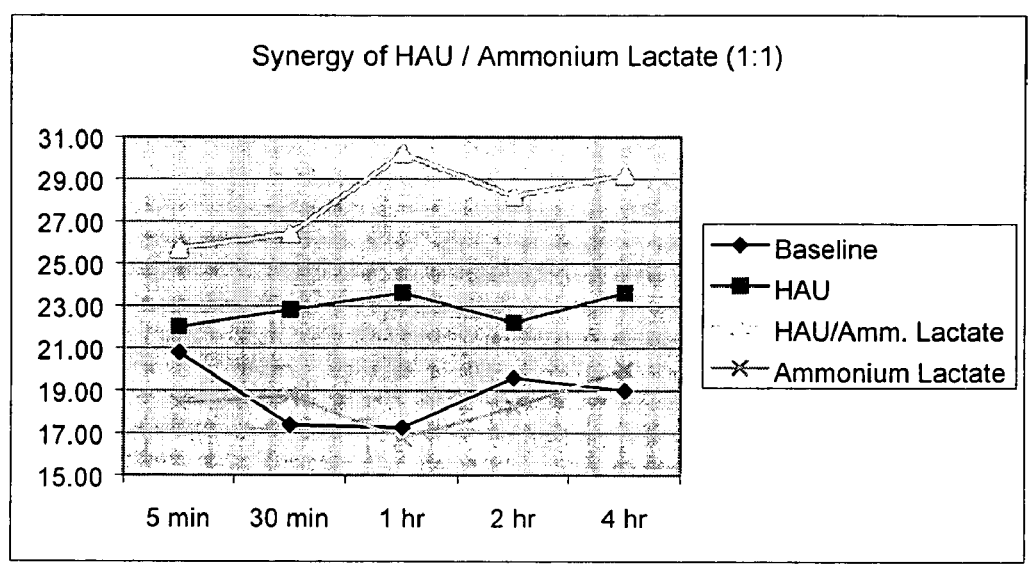
FIG. 2 depicts the relative skin moisture content of the synergy between hydroxyalkylurea and ammonium lactate at a ratio of 1:1.

In another study the active levels used for each individual agent were 5% HAU and 5% ammonium lactate, while the combination consisted of a total of 5% moisturizing ingredients at a ratio of 1:1 HAU to ammonium lactate. FIG. 2 shows the relative skin moisture content initially and at 5 minutes, 15 minutes, 1 hour, 2 hours, and 4 hours after application. Once again, the blend provides a significant increase in moisture over either individual moisturizing agent.

Example 2

Hydroxyethylurea and the moisturizing agent glycerin were analyzed alone and in combination. Active levels used for the individual agents were HAU at 15% and glycerin at 15%. The combination consisted of a total of 15% total moisturizing ingredients at a ratio of 1:1 of HAU:glycerin. Table 1 below shows the relative skin moisture content, initially and at 5 minutes, 15 minutes, 1 hour, and 2 hours after application. The blend showed a significant increase in moisture over either individual moisturizing agent.

TABLE 1

Relative Skin Moisture Content
Synergy of HAU/Glycerin (1:1) at 15% Active

|  | Initial | 5 min | 30 min | 1 hr | 2 hr |
|---|---|---|---|---|---|
| Baseline | 46.75 | 46.75 | 46.75 | 46.75 |  |
| HAU | 56.56 | 60.00 | 62.95 | 62.00 |  |
| Glycerin | 52.50 | 53.50 | 55.38 | 48.75 |  |
| Blend (1:1) | 88.25 | 73.00 | 71.25 | 70.00 |  |

Example 3

Figure 3:
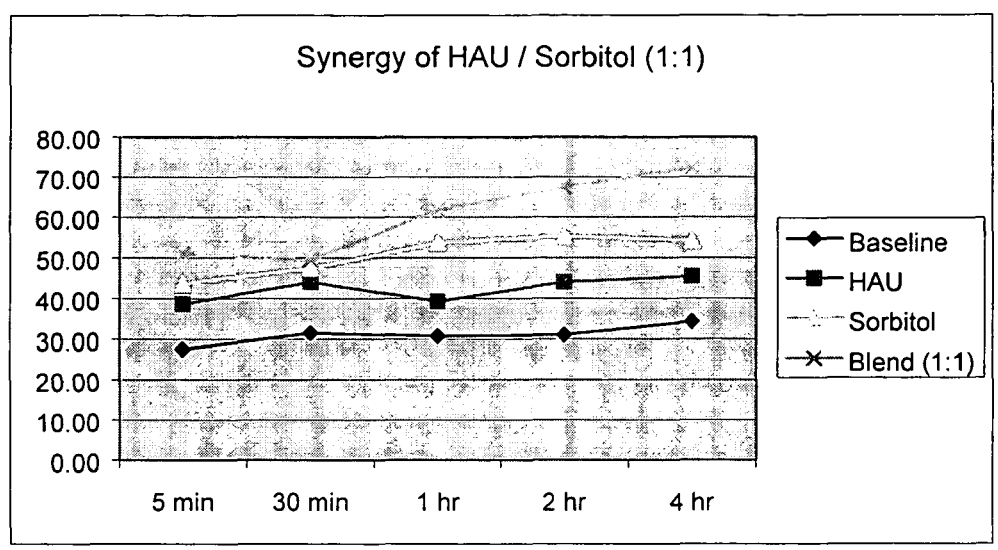
FIG. 3 depicts the relative skin moisture content of the synergy between hydroxyalkylurea and sorbitol at a ratio of 1:1.

Hydroxyethylurea and the moisturizing agent sorbitol were analyzed alone and in combination. Active levels used for the individual agents were HAU at 15% and Sorbitol at 15%. The combination consisted of a total of 15% total moisturizing ingredients at a ratio of 1:1 of HAU:Sorbitol. FIG. 3 illustrates the relative skin moisture content initially and at 5 minutes, 15 minutes, 1 hour, and 2 hour after application. From FIG. 3 it is seen that the blend provides a significant increase in moisture over either individual moisturizing agent, especially after 4 hours time.

Example 4

Hydroxyethylurea combined with ammonium lactate was compared to glycerin and a water blank for moisturization of hair. Active levels used for the test solutions were as follows: HAU and ammonium lactate together at 49% and 1%, respectively, glycerin at 50%, and the blank at 0%. Table 2 below provides the percent moisture uptake measured by DVS on hair after 4 and 20 hours.

TABLE 2

Percent moisture uptake by DVS analysis

| Product | 4 Hour @ 85% RH | 20 Hour @85% RH |
|---|---|---|
| Hydroxyethylurea and ammonium lactate | 18.72% | 47.65% |
| Glycerin | 22.10% | 44.58% |
| Blank (Water) | 13.58% | 14.53% |

Comparing the results of the hydroxyethylurea/ammonium lactate sample to the glycerin and blank samples in Table 2 shows that hydroxyethylurea is superior to the blank and similar or better than glycerin for bringing moisture to hair over time.

Example 5

A 49:1 blend of hydroxyethylurea (HAU) and ammonium lactate was compared to glycerin and a blank in the Controlled Humidity Hair Moisturization Analysis test described in Example 1. The results for % moisture gained are listed in Table 3 below.

TABLE 3

% Total Moisture Gained

| Sample | % Moisture Gained |
|---|---|
| HAU and ammonium lactate | 37.31 |
| Glycerin | 38.23 |
| Blank | 12.48 |

The results in Table 3 illustrate the moisturization benefits of the HAU/ammonium lactate blend. The blend performs similarly to glycerin and superior to the blank for moisturization.

Example 6

Clear Conditioning Shampoo Formula

| Ingredients | INCI Designation | % W/W | Supplier |
|---|---|---|---|
| CELQUAT SC-230M | Polyquaternium-10 | 0.25 | National Starch |
| Hydroxyethylurea | Not applicable | 3.00 | National Starch |
| Ammonium Lactate | Ammonium Lactate | 0.06 |  |
| DeIonized Water | Water (Aqua) | 18.18 |  |
| Standapol ES-2 | Sodium Lauryl Sulfate | 33.33 | Cognis Corp. |
| Standapol ES-3 | Sodium Laureth Sulfate | 30.00 | Cognis Corp. |
| Dehyton K | Cocamidopropyl Betaine | 10.00 | Cognis Corp. |
| Promodium CO | Polypropoxy-ethoxycocamide | 3.18 | Uniqema |
| Germaben II | Diazolidinyl Urea, Propylene Glycol, Methylparaben, Propylparaben | 1.00 | Sutton Laboratories |
| Sodium Chloride | Sodium Chloride | 1.00 | J. T. Baker |
| Citric Acid | Citric Acid | q.s. |  |
|  |  | 100.00 |  |

Procedure

CELQUAT SC-230M is dissolved in water by sifting into water slowly while mixing. In a separate vessel, all remaining ingredients are combined in the order listed above. The formulation is mixed until homogeneous after each addition. When both phases are homogeneous, the CELQUAT SC-230M phase is slowly added to the surfactant phase. The combined phases are then mixed with moderate agitation until homogeneous.

Example 6a

Example 6 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 7

6% VOC Root Lifting Aerosol Mousse Formula

| Ingredient | INCI Designation | % W/W | Supplier |
|---|---|---|---|
| Part A | | | |
| AMAZE | Corn Starch Modified | 2.20 | National Starch |
| CELQUAT H-100 | Polyquaternium-4 | 0.25 | National Starch |
| Carbopol Ultrez 10 | Acrylates/C10-30 Alkyl Acrylate Crosspolymer (copolymer) | 0.05 | Noveon |
| Natrosol HHR | Hydroxyethylcellulose | 0.15 | Aqualon |
| Deionized Water | Water (Aqua) | 70.32 | |
| TEA | Triethanolamine 99% | 0.05 | |
| Part B | | | |
| DC-193 | PEG-12 Dimethicone | 0.07 | Dow Corning |
| Versene 100 | Tetrasodium EDTA | 0.10 | Dow Chemical |
| Crovol Pk-70 | PEG-45 Palm Kernal Glycerides | 0.10 | Croda, Inc |
| Cropetide W | Hydrolyzed Wheat Protein (and) Hydrolyzed Wheat Starch | 0.20 | Croda. Inc. |
| Procetyl AWS | PPG-5 Ceteth-20 | 0.10 | Croda, Inc |
| dl-Panthenol | Panthenol | 0.10 | Ritapan |
| Reworteric AM B-14 | Cocomidapropyl Betaine | 0.05 | Goldschmidt |
| Tween 20 | Polysorbate 20 | 0.20 | Uniqema |
| Uvinul MS-40 | Benzephenone - 4 | 0.001 | BASF |
| Hydroxyethylurea | Hydroxyethyl Urea | 3.00 | National Starch |
| Ammonium Lactate | Ammonium Lactate | 0.06 | National Starch |
| Germaben II | Propylene Glycol (and) Diazolidinyl Urea (and) Methylparaben (and) Propylparaben | 1.00 | Sutton Labs |
| Part C | | | |
| DME | Dimethyl Ether | 6.00 | |
| Dymel 152A | Hydrofluorocarbon 152A | 16.00 | Dupont |
| | | 100.00 | |

Procedure

The Carbopol is slowly sifted into the mixing vortex until completely dispersed. While maintaining good agitation, the Natrosol HHR is then slowly sifted in. Once dispersed, both the AMAZE and the CELQUAT H-100 is sifted in. When the solution is complete, the TEA is added. The ingredients in Part B are then added and mixed until homogeneous. Filter and fill aerosol containers. For Part C, charge with propellant.

Example 7a

Example 7 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 8

Combing Cream for Dry/Damaged Hair Formula

| Ingredient | INCI Designation | % W/W | Supplier |
|---|---|---|---|
| Phase A | | | |
| Cetearyl Alcohol | 30/70 Cetearyl Alcohol | 1.80 | |
| Hostacerin CS200 | Ceteareth-20 | 0.20 | Clariant |
| Genamin KDMP | Behentrimonium Chloride | 0.44 | Clariant |
| DC 949 | Amodimethicone (and) Trideceth-12(and) Cetrimonium Chloride | 0.50 | Dow Corning |
| Phase B | | | |
| DI Water | Water (Aqua) | 88.94 | |
| STRUCTURE ZEA | Hydroxypropyl Starch Phosphate | 4.00 | National Starch |
| CELQUAT L-200 | Polyquaternium-4 | 0.40 | National Starch |
| Phase C | | | |
| Genamin CTAC 50 | Cetrimonium Chloride | 0.30 | Clariant |
| Phase D | | | |
| Glydant | DMDM Hydantoin | 0.20 | Lonza |
| Phenonip | Phenoxyethanol (and) Methylparaben (and) Ethylparaben (and) Butylparaben (and) Propylparaben (and) Isobutylparaben | 0.15 | Nipa/ Clariant |
| Hydroxyethylurea | Hydroxyethylurea | 3.00 | National Starch |
| Ammonium Lactate | Ammonium Lactate | 0.06 | |
| Phase E | | | |
| Citric acid (10%) | Citric Acid | q.s. | pH 4.0-5.0 |
| | | 100.00 | |

Procedure

Dissolve STRUCTURE ZEA into the water at room temperature. Add CELQUAT L-200 and heat to 80° C. while mixing (Phase B). In a separate vessel, combine Phase A and heat to 80° C. Add Phase B to Phase A with agitation. Add Phase C while maintaining temperature (80° C.). Continue mixing and cool to 45° C. Add Phase D and adjust pH, if necessary.

Example 8a

Example 8 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 9

Conditioning Styling Gel Formula

| Ingredient | INCI Designation | % W/W | Supplier |
|---|---|---|---|
| Part A | | | |
| Deionized Water | Water (Aqua) | 50.00 | |
| AMAZE XT | Dehydroxanthan Gum | 1.00 | National Starch |
| Part B | | | |
| Deionized Water | Water (Aqua) | 41.74 | |
| CELQUAT H-100 | Polyquaternium-4 | 0.15 | National Starch |
| Part C | | | |
| Propylene Glycol | Propylene Glycol | 2.00 | |
| DL-Panthenol | Panthenol | 0.50 | Roche |
| Na2EDTA | Disodium EDTA | 0.05 | |
| Hydroxyethylurea | Hydroxyethylurea | 3.00 | |
| Ammonium Lactate | Ammonium Lactate | 0.06 | |
| Cropeptide W | Hydrolyzed Wheat Protein and Hydrolyzed Wheat Starch | 1.00 | Croda |
| DC 193 | PEG-12 Dimethicone | 0.20 | Dow Corning |
| Glydant Plus Granular | DMDM Hydantoin and Iodopropynyl Butylcarbamate | 0.30 | |
| | | 100.00 | Lonza |

Procedure

Dust AMAZE XT into the water in Part A and mix until completely hydrated. Separately, combine the ingredients of Part B and mix until dissolved. Add Part B to Part A with agitation. Add remaining ingredients and mix until uniform.

Example 9a

Example 9 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 10

Leave-In Conditioner Formula

| Ingredients | INCI Designation | % W/W | Supplier |
|---|---|---|---|
| Phase A | | | |
| CELQUAT ® L-200 | Polyquaternium-4 | 0.30 | National Starch |
| Deionized Water | Water (Aqua) | 48.00 | |
| dl-Panthenol | Panthenol | 0.50 | Tri-K Industries |
| Phase B | | | |
| Deionized Water | Water (Aqua) | 44.79 | |
| TEA | Triethanolamine | 0.20 | |
| Neo Heliopan, Phenyl Type Hydro | Benzimidazole Sulfonic Acid | 0.20 | Haarmann & Reimer |
| DC 929 Cationic Emulsion | Amodimethicone (and) Tallowtrimonium Chloride (and) Nonoxynol-10 | 0.75 | Dow Corning |
| Phase C | | | |
| Solu-Silk Protein | Hydrolyzed Silk | 1.00 | Brooks Industries |
| Versene 100 | Tetra Sodium EDTA | 0.20 | Dow Chemical |
| Glydant | DMDM Hydantoin | 1.00 | Lonza |
| Hydroxyethylurea | Hydroxyethylurea | 3.00 | |
| Ammonium Lactate | Ammonium Lactate | 0.06 | |
| Fragrance | Fragrance (Perfume) | q.s. | |
| | | 100.00 | |

Preparation

Prepare Phase A by dispersing and dissolving CELQUAT L-200 in water using good agitation. Mix until solution is clear and homogenous. Add dl-Panthenol and allow to completely dissolve. Prepare Phase B by adding TEA to water and mix well. Add Neo Heliopan and mix until clear. Follow with DC 929 cationic emulsion. Combine parts by adding Phase B to Phase A. Mix well and continue to mix for approximately 15 minutes. Add Solu-silk and mix well. Add Versene 100, Glydant, hydroxyethylurea, ammonium lactate, and fragrance, mixing well after each addition.

Example 10a

Example 10 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N- bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 11

Clear Conditioner With Suspended Beads

| Ingredients | INCI Designation | % W/W | Supplier |
|---|---|---|---|
| Phase A | | | |
| Deionized Water | Water (Aqua) | 78.74 | |
| CELQUAT H-100 | Polyquaternium-4 | 0.25 | National Starch |
| Glydant | DMDM Hydantoin | 0.50 | Lonza |
| Propylene Glycol | Propylene Glycol | 2.00 | |
| Arquad 16-25W | Cetrimonium Chloride | 2.00 | Akzo-Nobel |
| STRUCTURE PLUS | Acrylates/Aminoacrylates/C10-30 Alkyl PEG-20 Itaconate Copolymer | 10.00 | National Starch |
| Hydroxyethylurea | Hydroxyethylurea | 3.00 | |
| Ammonium Lactate | Ammonium Lactate | 0.06 | |
| Versene 100 | Tetrasodium EDTA | 0.05 | Dow Chemical |
| Phase B | | | |
| Silsoft A-858 | Dimethicone Copolyol Bishydroxyethylamine | 2.00 | CK Witco OSI |
| Neo Heliopan AV | Ethylhexyl Methoxycinnamate | 0.05 | Haarman & Reimer |
| Phase C | | | |
| Glycolic Acid (70%) | Glycolic Acid | 0.45 | |
| Phase D | | | |
| Florabeads | Jojoba Esters | 0.80 | Floratech |
| | | 100.00 | |

Procedure

Polyquaternium-4 is dissolved in water with mixing. The remaining ingredients of Phase A are sequentially added with continued mixing. Phase B is combined and then added to Phase A. Continue to mix while slowly adding glycolic acid to Phase AB, taking care to avoid entrapped air. Finally, add beads slowly while mixing.

Example 11a

Example 11 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 12

Natural Hold Styling Lotion Formula

| Ingredient | INCI Designation | % W/W | Supplier |
|---|---|---|---|
| Phase A | | | |
| Deionized Water | Water (Aqua) | 72.94 | |
| STRUCTURE XL | Hydroxypropyl Starch Phosphate | 5.00 | National Starch |
| Phenochem | Phenoxyethanol, Methylparaben, Ethylparaben, Propylparaben, Butylparaben, Isobutylparaben | 1.00 | Sharon Labs/ S Black Ltd |
| AMAZE | Corn Starch Modified | 3.00 | National Starch |
| Hydroxyethylurea | Hydroxyethylurea | 3.00 | |
| Ammonium Lactate | Ammonium Lactate | 0.06 | |
| Phase B | | | |
| Imwitor 380 | Glyceryl Cocoate/ Citrate/Lactate (E472c/E472b) | 5.00 | Sasol/ S Black Ltd |
| Jojoba Glaze LV | Buxus Chinensis, Hydrogenated Ethylene/ propylene/styrene Copolymer, Hydrogenated Butylene/ Ethylene/styrene Copolymer, BHT | 10.00 | DWJ/ S Black Ltd |
| | | 100.00 | |

Procedure

Premix Phase A for 20 minutes. Premix Phase B. Phase B is then added to Phase A with high speed mixing.

Example 12a

Example 12 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2- hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 13

55% VOC Firm Hold, Crystal Clear Pump Hair Spray Formula

| Ingredients | INCI Designation | % W/W | Supplier |
|---|---|---|---|
| BALANCE 0/55 | Acrylates Copolymer | 12.00 | National Starch |
| AMP (reg) | Aminomethyl Propanol | 0.85 | Dow Chemical |
| Deionized Water | Water (Aqua) | 29.09 | |
| Hydroxyethylurea | Hydroxyethylurea | 3.00 | |
| Ammonium Lactate | Ammonium Lactate | 0.06 | |
| *SD Alcohol 40 | SD Alcohol 40 | 55.00 | |
| | | 100.00 | |

Preparation

Dissolve AMP in SD Alcohol 40 and water. While maintaining proper agitation, slowly pour in BALANCE 0/55. Add remaining ingredients and mix until homogenous.

Example 13a

Example 13 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 14

Curl Defining Combing Cream Formula

| Ingredient | INCI Designation | % W/W | Supplier |
|---|---|---|---|
| Phase A | | | |
| Cetearyl Alcohol | Cetearyl Alcohol | 2.20 | |
| Hostacerin CS 200 | Ceteth-20 | 0.30 | Clariant |
| Phase B | | | |
| DI Water | Water (Aqua) | 82.30 | |
| STRUCTURE ZEA | Hydroxypropyl Starch Phosphate | 2.00 | National Starch |
| Phase C | | | |
| Genamin CTAC | Cetrimonium Chloride | 2.00 | Clariant |
| Phase D | | | |
| DI Water | Water (Aqua) | 6.94 | |
| DynamX | Polyurethane-14 (and) AMP Acrylates Copolymer | 0.50 | National Starch |

-continued

| Ingredient | INCI Designation | % W/W | Supplier |
|---|---|---|---|
| Glydant | DMDM Hydantoin | 0.70 | Lonza |
| Hydroxyethyurea | Hydroxyethylurea | 3.00 | |
| Ammonium Lactate | Ammonium Lactate | 0.06 | |
| Phase E | | | |
| Citric Acid | Citric Acid | q.s. to pH 4.0-5.0 | |
| | | 100.00 | |

Preparation

Dissolve STRUCTURE ZEA into the water at room temperature (Phase B). Heat it to 80° C. Melt the components of Phase A (80° C.) and stir into Phase B, under agitation. Add Phase C. Keep the temperature for 15 minutes. Cool to 60° C. and add Phase D. Continue mixing until cool and then perform pH adjustment.

Example 14a

Example 14 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 15

Smooth Move Anti-Frizz Lotion Formula

| Ingredient | INCI Designation | % W/W | Supplier |
|---|---|---|---|
| Phase A | | | |
| Deionized Water | Water (Aqua) | 81.85 | |
| EDTA Na2 | Disodium EDTA | 0.15 | Dow |
| STRUCTURE XL | Hydroxypropyl Starch Phosphate | 5.00 | National Starch |
| Germaben II | Propylene Glycol, Diazolidinyl Urea, Methylparaben, Propylparaben | 1.00 | Sutton |
| FLEXAN II | Sodium Polystyrene Sulfonate | 3.00 | National Starch |
| Hydroxyethyurea | Hydroxyethylurea | 3.00 | National Starch |
| Ammonium Lactate | Ammonium Lactate | 0.06 | National Starch |
| Phase B | | | |
| Caprylic/capric Triglyceride | Caprylic/capric Triglyceride | 5.00 | |
| Monasil PCA | PCA Dimethicone | 2.00 | Uniqema |
| DC 193 | PEG-12 Dimethicone | 2.00 | Dow Corning |
| | | 100.00 | |

Preparation

Dissolve STRUCTURE XL in water, stirring for ten minutes (400 rpm). Add the rest of ingredients of Phase A. Separately mix ingredients of Phase B. Slowly add Phase B to Phase A while stirring intensively (500-600 rpm).

Example 15a

Example 15 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 16

Clear Conditioning Shampoo Formula

| Ingredients | INCI Designation | % W/W | Supplier |
|---|---|---|---|
| CELQUAT SC-230M | Polyquaternium-10 | 0.25 | National Starch |
| Hydroxyethylurea | Not applicable | 3.00 | National Starch |
| DeIonized Water | Water (Aqua) | 18.24 | |
| Standapol ES-2 | Sodium Lauryl Sulfate | 33.33 | Cognis Corp. |
| Standapol ES-3 | Sodium Laureth Sulfate | 30.00 | Cognis Corp. |
| Dehyton K | Cocamidopropyl Betaine | 10.00 | Cognis Corp. |
| Promodium CO | Polypropoxy-ethoxycocamide | 3.18 | Uniqema |
| Germaben II | Diazolidinyl Urea, Propylene Glycol, Methylparaben, Propylparaben | 1.00 | Sutton Laboratories |
| Sodium Chloride | Sodium Chloride | 1.00 | J. T. Baker |
| Citric Acid | Citric Acid | q.s. | |
| | | 100.00 | |

Procedure

CELQUAT SC-230M is dissolved in water by sifting into water slowly while mixing. In a separate vessel, all remaining ingredients are combined in the order listed above. The formulation is mixed until homogeneous after each addition. When both phases are homogeneous, the CELQUAT SC-230M phase is slowly added to the surfactant phase. The combined phases are then mixed with moderate agitation until homogeneous.

Example 16a

Example 16 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Example 17

Leave-In Conditioner Formula

| Ingredients | INCI Designation | % W/W | Supplier |
|---|---|---|---|
| Phase A | | | |
| CELQUAT ® L-200 | Polyquaternium-4 | 0.30 | National Starch |
| Deionized Water | Water (Aqua) | 48.06 | |
| dl-Panthenol | Panthenol | 0.50 | Tri-K Industries |
| Phase B | | | |
| Deionized Water | Water (Aqua) | 44.79 | |
| TEA | Triethanolamine | 0.20 | |
| Neo Heliopan, Type Hydro | Phenyl Benzimidazole Sulfonic Acid | 0.20 | Haarmann & Reimer |
| DC 929 Cationic Emulsion | Amodimethicone (and) Tallowtrimonium Chloride (and) Nonoxynol-10 | 0.75 | Dow Corning |
| Phase C | | | |
| Solu-Silk Protein | Hydrolyzed Silk | 1.00 | Brooks Industries |
| Versene 100 | Tetra Sodium EDTA | 0.20 | Dow Chemical |
| Glydant | DMDM Hydantoin | 1.00 | Lonza |
| Hydroxy-ethylurea | Hydroxyethylurea | 3.00 | |
| Fragrance | Fragrance (Perfume) | q.s. | |
| | | 100.00 | |

Preparation

Prepare Phase A by dispersing and dissolving CELQUAT L-200 in water using good agitation. Mix until solution is clear and homogenous. Add dl-Panthenol and allow to completely dissolve. Prepare Phase B by adding TEA to water and mix well. Add Neo Heliopan and mix until clear. Follow with DC 929 cationic emulsion. Combine parts by adding Phase B to Phase A. Mix well and continue to mix for approximately 15 minutes. Add Solu-silk and mix well. Add Versene 100, Glydant, hydroxyethylurea and fragrance, mixing well after each addition.

Example 17a

Example 17 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2- hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N'-bis-(2-hydroxypropyl) urea.

Example 18

Combing Cream For Dry/Damaged Hair Formula

| Ingredient | INCI Designation | % W/W | Supplier |
|---|---|---|---|
| Phase A | | | |
| Cetearyl Alcohol | 30/70 Cetearyl Alcohol | 1.80 | |
| Hostacerin CS200 | Ceteareth-20 | 0.20 | Clariant |
| Genamin KDMP | Behentrimonium Chloride | 0.44 | Clariant |
| DC 949 | Amodimethicone (and) Trideceth-12(and) Cetrimonium Chloride | 0.50 | Dow Corning |
| Phase B | | | |
| DI Water | Water (Aqua) | 89.00 | |
| STRUCTURE ZEA | Hydroxypropyl Starch Phosphate | 4.00 | National Starch |
| CELQUAT L-200 | Polyquaternium-4 | 0.40 | National Starch |
| Phase C | | | |
| Genamin CTAC 50 | Cetrimonium Chloride | 0.30 | Clariant |
| Phase D | | | |
| Glydant | DMDM Hydantoin | 0.20 | Lonza |
| Phenonip | Phenoxyethanol (and) Methylparaben (and) Ethylparaben (and) Butylparaben (and) Propylparaben (and) Isobutylparaben | 0.15 | Nipa/ Clariant |
| Hydroxyethylurea | Hydroxyethylurea | 3.00 | National Starch |
| Phase E | | | |
| Citric acid (10%) | Citric Acid | q.s. | pH 4.0-5.0 |
| | | 100.00 | |

Procedure

Dissolve STRUCTURE ZEA into the water at room temperature. Add CELQUAT L-200 and heat to 80° C. while mixing (Phase B). In a separate vessel, combine Phase A and heat to 80° C. Add Phase B to Phase A with agitation. Add Phase C while maintaining temperature (80° C.). Continue mixing and cool to 45° C. Add Phase D and adjust pH, if necessary.

Example 18a

Example 18 is repeated with, in place of hydroxyethylurea, any one of the following hydroxyalkyl-substituted ureas: N-(2-hydroxypropyl), N-(3-hydroxypropyl), N-(2,3-dihydroxypropyl), N-(2-hydroxybutyl), N-(3-hydroxypropyl), N-(4-hydroxybutyl), N-(2,3-dihydroxybutyl), N-(2,4-dihydroxybutyl), N-(3,4-dihydroxybutyl), N-ethyl-N'-(2-hydroxyethyl), N,N-bis-(2-hydroxyethyl), N,N'-bis-(2-hyroxyethyl), N,N-bis-(2-hydroxypropyl), N,N'-bis-(2-hydroxypropyl), N,N-bis-(2-hydroxyethyl)-N'-propyl, N,N-bis-(2-hydroxypropyl)-N'-(2-hydroxyethyl), N-tert.-butyl-N'-(2-hydroxyethyl)-N'-(2-hydroxypropyl), N,N-bis-(2-hydroxyethyl)-N',N'-dimethyl, N,N,N',N'-tetrakis-(2-hydroxyethyl), and N,N-bis(2-hydroxyethyl)-N',N'-bis-(2-hydroxypropyl) urea.

Although the present invention has been described and illustrated in detail, it is to be understood that the same is by way of illustration and example only, and is not to be taken as a limitation. The spirit and scope of the present invention are to be limited only by the terms of any claims presented hereafter.

We claim:

1. A personal care composition comprising:
   at least one hydroxyalkyl urea derived from urea and of the general formula

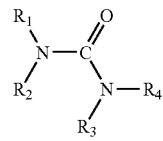

wherein $R^1$, $R^2$, $R^3$ and $R^4$ each independently represent hydrogen, a $C_{1-4}$ alkyl or a $C_{2-6}$ hydroxyalkyl group having from 1 to 5 hydroxyl or hydroxyalkyl groups, provided that at least one of the radicals R1-R4 is a hydroxyalkyl or oligohydroxyalkyl group; and
   at least one ammonium salt comprising ammonium lactate;
   wherein the hydroxyalkyl urea and the ammonium salt are present in a synergistically moisturizing effective ratio; and
   wherein the combination of the hydroxyalkyl urea and the ammonium salt provide an increase in moisturization greater than either the at least one hydroxyalkyl urea or the ammonium salt alone.

2. The composition of claim 1, wherein the ratio of hydroxyalkylurea to the at least one ammonium salt is at least about 1:5 and no more than about 5:1.

3. The composition of claim 1, wherein the hydroxyalkyl urea is N-2-hydroxyethylurea.

4. The composition of claim 1, wherein the hydroxyalkylurea is present in an amount of from about 0.5% to 15.0% by weight of the personal care composition.

5. The composition of claim 1 wherein the hydroxyalkylurea is present in an amount of from about 1 to about 8% by weight of the personal care composition.

6. The personal care composition of claim 1, further comprising at least one moisturizing agent selected from the group consisting of petrolatum, mineral and vegetable oils, lanolins, glycerin, sorbitol, polyols, urea, lactic acid, lactates, sugars, alpha hydroxy acids, beta hydroxy acids, sodium hyaluronate, hyaluronic acid, pyrrolidone carboxylic acid, and combinations thereof.

7. The composition of claim 1, wherein the at least one ammonium salt is present in an amount of from about 0.5% to 15% by weight of the personal care composition.

8. The composition of claim 1, wherein the at least one ammonium salt is present in an amount of from about 1% to about 10% by weight of the personal care composition.

9. The composition of claim 1, wherein the at least one ammonium salt is present in an amount of from about 2% to about 6% by weight of the personal care composition.

10. The composition of claim 1, wherein the hydroxyalkyl urea is N-2-hydroxyethylurea and the composition further comprises at least one moisturizing agent selected from the group consisting of petrolatum, mineral and vegetable oils, lanolins, glycerin, sorbitol, polyols, urea, lactic acid, lactates, sugars, alpha hydroxy acids, beta hydroxy acids, sodium hyaluronate, hyaluronic acid, pyrrolidone carboxylic acid, and combinations thereof.

11. A skin care composition comprising the composition of claim 1.

12. A hair product comprising the composition of claim 1.

13. The hair product of claim 12 wherein the hair product is selected from the group consisting of hair gel, hair lotion, hair cream, mousse, shampoo, conditioner and hair spray.

14. A conditioner comprising the composition of claim 1.

15. The conditioner of claim 14 wherein the conditioner is a leave-on conditioner.

16. The conditioner of claim 14 wherein the conditioner is a hair or skin conditioner.

* * * * *